United States Patent
Scepanski

(10) Patent No.: US 6,518,313 B1
(45) Date of Patent: Feb. 11, 2003

(54) SOLID SANITIZERS AND CLEANER DISINFECTANTS

(75) Inventor: William H. Scepanski, Bloomington, MN (US)

(73) Assignee: Sunburst Chemicals, Inc., Minneapolis, MN (US)

(*) Notice: Subject to any disclaimer, the term of this patent is extended or adjusted under 35 U.S.C. 154(b) by 0 days.

(21) Appl. No.: 09/779,910

(22) Filed: Feb. 8, 2001

Related U.S. Application Data

(63) Continuation of application No. 09/295,039, filed on Apr. 20, 1999, now abandoned, which is a continuation of application No. 08/534,664, filed on Sep. 27, 1995, now Pat. No. 6,028,113.

(51) Int. Cl.$^7$ .................. A01N 33/12; A01N 47/28; B01D 11/02; C11D 1/62; B67D 5/00

(52) U.S. Cl. ............... 514/642; 514/588; 514/643; 514/772; 514/772.3; 514/964; 514/975; 424/78.08; 424/401; 424/405; 424/409; 424/486; 424/DIG. 5; 422/28; 422/34; 422/37; 422/261; 422/266; 422/278; 510/382; 510/391; 510/445; 510/447; 510/504; 504/150; 504/158; 137/268; 222/190

(58) Field of Search ............... 422/266, 261, 422/278, 28, 34, 37; 424/409, 78.08, 401, 405, 486, DIG. 5; 514/642, 643, 588, 772, 772.3, 964, 975; 510/382, 391, 445, 447, 504; 504/150, 158; 137/268; 222/190

(56) References Cited

U.S. PATENT DOCUMENTS

| | | | |
|---|---|---|---|
| 3,519,414 A | 7/1970 | Nikawitz et al. | 504/130 |
| 3,827,873 A | 8/1974 | Shema et al. | 504/148 |
| 4,028,261 A | 6/1977 | Petersen et al. | 134/42 |
| 4,624,713 A | 11/1986 | Morganson et al. | 134/25.2 |
| 4,769,159 A | 9/1988 | Copeland | 252/8.8 |
| 5,312,624 A | 5/1994 | Richter et al. | 424/405 |
| 5,342,587 A * | 8/1994 | Laughlin et al. | 422/266 |
| 5,358,653 A | 10/1994 | Gladfelter et al. | 252/90 |
| 5,419,908 A | 5/1995 | Richter et al. | 424/405 |
| 5,435,157 A | 7/1995 | Laughlin | 68/17 R |
| 5,462,681 A | 10/1995 | Gutzmann et al. | 252/11 |
| 5,474,698 A | 12/1995 | Rolando et al. | 252/90 |
| 5,478,537 A | 12/1995 | Laughlin et al. | 422/266 |
| 5,622,708 A | 4/1997 | Richter et al. | 623/8 |
| 5,674,831 A | 10/1997 | Schultz et al. | 510/501 |
| 5,698,513 A | 12/1997 | Schultz et al. | 510/501 |
| 5,709,871 A | 1/1998 | Hill | 424/409 |
| 5,837,651 A | 11/1998 | Hill | 504/116 |
| 6,028,113 A | 2/2000 | Scepanski | 514/643 |
| 6,060,444 A * | 5/2000 | Schulz et al. | 510/451 |
| 6,197,321 B1 * | 3/2001 | Richter et al. | 424/409 |
| 6,395,703 B2 * | 5/2002 | Scepanski | 510/445 |

OTHER PUBLICATIONS

Encyclopedia of Chemical Technology, Fourth Edition; Kirk–Othmer, vol. 8, A Wiley–Interscience Publication, Nov. 1993.

Armak Technical Data Sheet—Doumeen, Armack Company, Bull 81–19, pp. 1–4, 1981.

Lonza Product Information—Bardac, Jul., 1982.

Huntington H&S Chemicals Division, Formulation HTA–64 Disinfectant, Feb. 1990.

Huntington H&S Chemicals Division, Formulation HS–8451P Disinfectant–Deodorant, May, 25, 1989.

Huntington H&S Chemicals Division, Formulation RTU–6075, Apr. 1989.

Huntington H&S Chemicals Division, Formulation HWS–128 Germicidal Detergent & Deodorant, Nov. 1989.

\* cited by examiner

*Primary Examiner*—John Pak
(74) *Attorney, Agent, or Firm*—Patterson, Thuente, Skaar & Christensen

(57) ABSTRACT

Solid sanitizing compositions have advantages over corresponding liquids and powders. A solid sanitizing product can be contained within a plastic bottle with a label indicating that the contents have antimicrobial or deodorizing properties containing a non-flowable solid composition having greater than about 0.02 percent by weight antimicrobial compounds. The preferred solid sanitizing compositions consist essentially of an antimicrobial compound selected from the group consisting of quaternary ammonium salts, fatty amines and diamines, chlorhexidine gluconate, phenol, derivatives of phenol, parachloro metaxylenol and mixtures thereof, and between 0 and 99.98 percent by weight of a cleaning composition. The solid sanitizing compositions can be effectively used with solid dispensers. The solid dispensers have a bowl with a drain at the bottom and an upward pointing spray nozzle. The spray nozzle directs water into an inverted bottle of the sanitizing composition to produce an aqueous solution of sanitizing compounds which drains from the bottom of the bowl. A second source of aqueous solution or fresh water can combine with the solution draining from the bowl to product a more dilute solution of sanitizing compounds. The relative flow into the spray nozzle and the secondary source can be adjusted to produce a final diluted solution with a desired dilution. Antimicrobial solutions can be used in a variety of industrial and institutional applications including laundry and hard surface cleaning. Four methods of producing the solid sanitizing compositions are described.

24 Claims, 1 Drawing Sheet

SOLID SANITIZERS AND CLEANER DISINFECTANTS

This is a Continuation Division of Application Ser. No. 09/295,039 filed Apr. 20, 1999, now abandoned, which in turn is a continuation of Application Ser. No. 08/534,664 filed Sep. 27, 1995, now U.S. Pat. No. 6,028,113, issued Feb. 22, 2000.

FIELD OF THE INVENTION

The invention relates to solid compositions containing antimicrobial agents. The invention more specifically relates to non-flowing solids containing particular antimicrobial agents where the solids can be used in dispensers which direct water at the surface of the solid to dissolve a selected amount of the solid to produce a sanitizing, deodorizing or disinfecting solution.

BACKGROUND OF THE INVENTION

An extensive number of antimicrobial compositions are commercially available in liquid or power form. The liquid compositions typically have active ingredients in the range of 5 percent to 15 percent by weight of the product, but highly concentrated liquid products can contain up to 80% active ingredients. Concentrated liquid products must be diluted before use. Ready to use liquid products can have concentrations of active ingredients at least as low as 0.02 percent by weight of the product. All of these liquid products contain significant amounts of water, alcohols and/or other materials as diluents. Because these products are diluted, they utilize more packaging materials and result in higher shipping weights to transport a given amount of active material than is required for a highly concentrated solid.

A significant disadvantage of powder or granular products for commercial applications is that they are not as accurately controllable in dispensing equipment as liquids. Powder systems can require manually scooping a quantity of powder for each use, thus not taking advantage of the ease, accuracy and hands-off labor savings of liquid dispensers. Also, powders can cake if exposed to high humidity or temperatures. Once they become caked, they cannot be easily removed from their shipping container. Non-homogeneous powders can segregate in their shipping containers, in other words, separate or stratify by particle size or density, resulting in non-uniform mixture that may not be appropriate for ultimate use applications.

Some disinfectants and sanitizers are considered corrosive which creates hazards in shipping and handling. Spilled liquid material from leaking containers or mishandling the product can come into contact with skin or eyes causing tissue damage, pain and discomfort. Powders can create a safety hazard because particles of irritating or corrosive materials can exit their container or become airborne allowing the particles to come into direct contact with tissue, such as skin or lungs, causing burns or discomfort. A solid antimicrobial product would not be easily capable of creating this hazard since it cannot leak out of its container nor can it be spilled in handling.

Because of stringent regulatory controls over disinfectants and sanitizers especially for institutional uses, solutions for application typically must be prepared with specific and exacting dilution ratios. Typical sanitizers and disinfectants concentrates are mixed with water to obtain a solution with a specific concentration for applications. These solutions are used to sanitize or disinfect objects and surfaces such as counter tops, tables, floors, walls, dishes, utensils and fabrics. Many institutions require these products including food processing operations, nursing homes, health care facilities, kitchens, and laundries. Here, the terms disinfectant and sanitizer are used interchangeably to denote an antimicrobial agent even though the terms may have precise and distinct meanings in institutional use and under regulatory control These products are also effective at deodorizing because they can destroy odor causing bacteria and other microbes.

While liquid and powder products can be measured by hand and accurately diluted, this process is slow and potentially hazardous if the materials are corrosive. Liquid products can be properly diluted using dispensing apparatuses to product solutions for application, but this does not eliminate all of the inconveniences and hazards of the handling of liquid. Recently, dispensers have been developed for the accurate and convenient dispensing of solids. For example, U.S. Pat. No. 5,342,587 to Laughlin et al. describes a solid dispensing device where the solid is provided in a plastic bottle that is inverted over a bowl. Water is sprayed on the solid to produce a solution that is drained from the bowl.

Some sanitizer or disinfectant concentrates have cleaning agents added to the antimicrobial compounds to create cleaner/disinfectants. Commercially available liquid and powder cleaner/disinfectants clean soils from surfaces as well as kill microorganisms. The cleaning agents in these products are typically alkaline and include anionic or non-ionic surfactants along with other additives such as alkaline builders and metal ion sequestering agents. Liquid and powder cleaner/disinfectants have the same disadvantage as liquid and powder forms of other sanitizing products.

SUMMARY OF THE INVENTION

Solid sanitizing compositions avoid the deficiencies of either liquids or powders. The solids provide for convenient and safe handling and can be dispensed accurately and conveniently using solid dispensers. The preferred solid sanitizing products are in a plastic container, such as a bottle or jar, with a label indicating that the contents have antimicrobial properties. The container will contain a non-flowable solid including greater than about 0.02 percent by weight antimicrobial compounds. The solid will preferably contain greater that about 0.5 percent by weight antimicrobial compounds, more preferably greater than 2 percent by weight antimicrobial compounds and even more preferably greater than 5 percent by weight antimicrobial compounds.

The antimicrobial compounds are preferably selected from the group consisting of quaternary ammonium salts, fatty amines and diamines, chlorhexidine gluconate, phenol, derivative of phenol, parachloro metaxylenol and mixtures thereof. The quaternary ammonium salts will preferably have at least one alkyl substituent on the quaternary nitrogen with $C_6$ to $C_{18}$ hydrocarbon units.

The preferred amines and diamines have at least one alkyl substituent with carbon chain lengths in the range of $C_{10}$–$C_{18}$.

The preferred solid sanitizing compositions consist essentially of greater than about 0.02 percent weight of an antimicrobial compound and between 0 and 99.98 percent of a cleaning composition. The cleaning composition can be alkaline or neutral pH. The cleaning compositions preferably comprise compounds selected from the group consisting of surfactants, alkaline builders and polyvalent metal sequestering agents.

The invention also includes methods of using and methods of making solid sanitizing compositions. One preferred method of using a solid sanitizing composition of the invention involves producing an antimicrobial use solution using a dispenser comprising a bowl with a drain, a tube connected to the drain and a spray nozzle for directing water up from the bowl. An open bottle containing a solid sanitizing composition is inverted into the bowl such that water from the spray nozzle is directed into the open bottle. The spray of water dissolves a portion of the sanitizing composition to form an aqueous solution of antimicrobial compounds. The resulting antimicrobial solutions can be used particularly in a variety of industrial and institutional applications including laundry and hard surface cleaning. The solid antimicrobial composition preferably comprises greater than about 0.02 percent by weight of antimicrobial compound selected from the group consisting of quaternary ammonium salts, fatty amines and diamines, chlorhexidine gluconate, phenol, derivatives of phenol, parachloro metaxylenol and mixtures thereof.

Another preferred method of using a solid sanitizing composition of the invention involves producing an antimicrobial use solution using a dispenser having a bowl with a drain at the bottom of the bowl, a spray nozzle for directing water upward from the bowl, a tube connected to the opening of the drain and an aqueous solution supply connecting with the tube from the drain to form a combined flow. A bottle containing a solid antimicrobial composition is inverted into the bowl of the dispenser. The spray nozzle is directed upward into the open bottle of the solid antimicrobial composition. The relative flow volumes into the spray nozzle and the aqueous solution supply are adjusted to produce a desired concentration of antimicrobial, deodorizing solution in the combined flow.

There are several methods of producing the solid sanitizing compositions. The first method involves forming a melted composition consisting essentially of antimicrobial compounds and between 0 and 99.98 percent by weight of an alkaline cleaning composition. The solid sanitizing composition preferably comprises greater than 0.02 percent by weight antimicrobial compounds and more preferably greater than about 1 percent by weight antimicrobial compounds. The melted composition is poured into a container where it solidifies upon cooling.

A second method of producing solid sanitizing compositions involves heating a solution of antimicrobial compounds to remove sufficient solvent to form a solvent depleted composition. The solvent depleted composition is poured into a container. The solvent depleted composition cools to form a non-flowable composition. A solvent depleted composition is a composition that will cool to form a non-flowable material upon cooling.

A third method of producing solid sanitizing compositions begins by melting a solid carrier. A powder antimicrobial composition is mixed into the melted carrier to form a melted antimicrobial composition. The melted antimicrobial composition is poured into a container. Upon cooling to room temperature, the composition forms a solid antimicrobial composition.

The fourth method of producing a solid sanitizing composition involves mixing an aqueous solution of an antimicrobial compound with an anhydrous hydratable salt to form a homogeneous dispersion. The aqueous solution of the antimicrobial compound can be preformed or it can be formed in situ by adding a powder antimicrobial compound and water or another aqueous solution. The compounds in the homogenous solution may or may not be dissolved. The homogeneous dispersion is poured into a container. The container is stored until a solid composition is formed in the container.

DETAILED DESCRIPTION OF THE INVENTION

Figure 1:
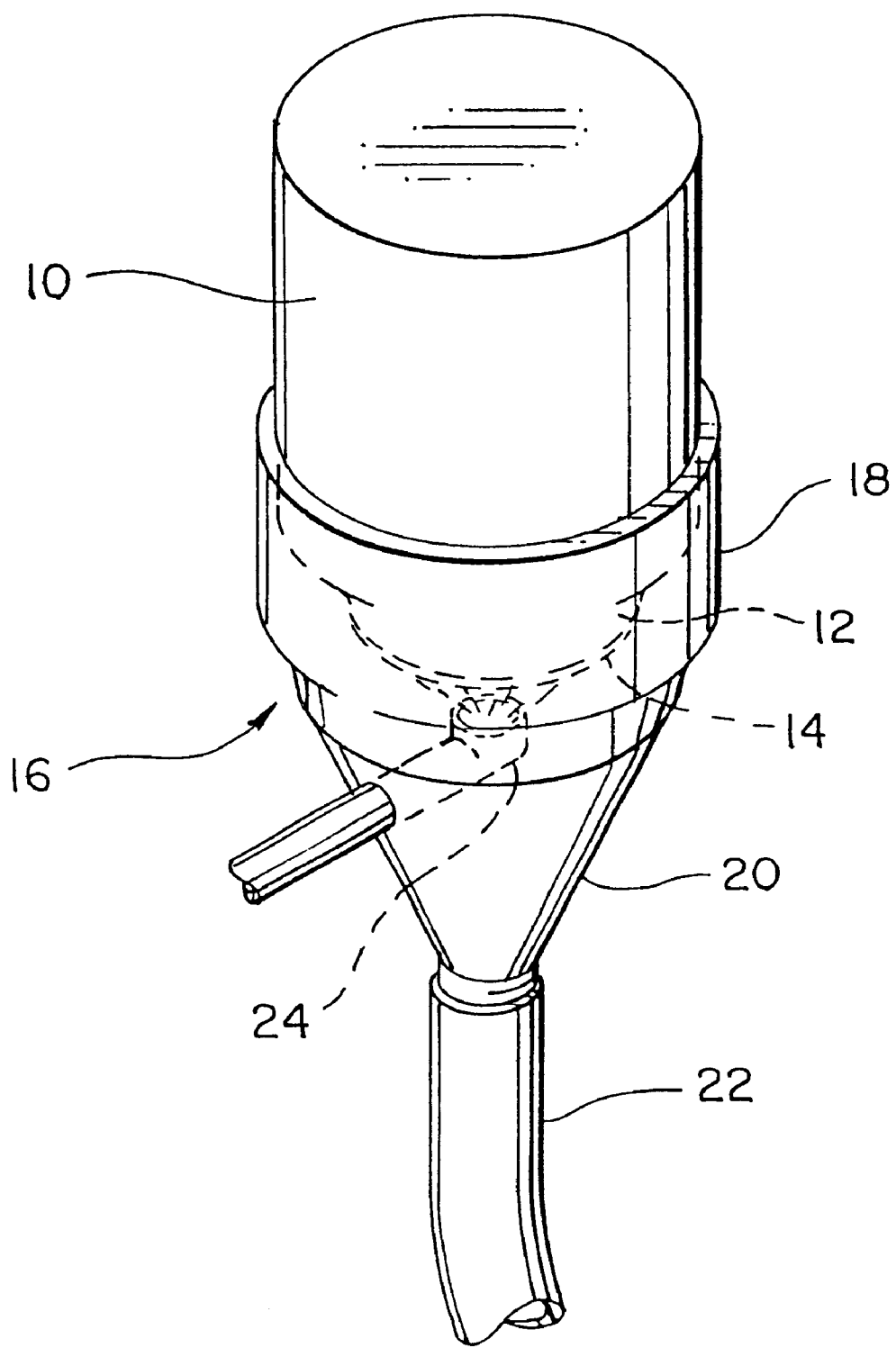
FIG. 1 is a schematic representation of a dispenser with a container filled with a composition within the invention, where a nozzle for directing water into the open end of the container within the dispenser is shown in broken lines.

The invention consists of antimicrobial compositions manufactured into a solid form. It is preferred that the solid be produced in a container, e.g., a bottle or jar, such that the container can be used with a solid dispenser. In a typical solid dispenser, the container containing the solid is inverted in the dispenser, and the dispenser directs water at the surface of the solid to produce a solution having the particular concentration of the antimicrobial compounds. The solution can be further diluted if necessary. The invention is founded on the surprising simplicity of producing these solid products in a practical manner using particular types of antimicrobials. The solid sanitizers, deodorizers and disinfectant/cleaners of the invention are particularly suitable to use in recently developed dispensers.

The antimicrobial compounds are preferably U.S. Environmental Protection Agency approved for use as sanitizers or disinfectants. Appropriate antimicrobial agents include quaternary ammonium compounds, fatty amines and diamines, chlorhexidine gluconate, phenol and halogen or methyl substituted phenols, parachlorometa xylenol although this list is not inclusive. The antimicrobial compound or mixture of antimicrobial compounds will comprise 0.02 percent of 100 percent of the solid product by weight. More preferably, the solid product will contain 0.5 percent to 100 percent of the antimicrobial compounds. Even more preferably, the solid product will contain between 2 percent and 100 percent of the antimicrobial compounds. Generally, the appropriate antimicrobial compounds are selected from the group consisting of quaternary ammonium salts, fatty amines and diamines, chlorhexidine gluconate, phenol, derivatives of phenol, parachloro metaxylenol and mixtures thereof.

Appropriate commercially available quaternary ammonium compounds with antimicrobial properties include n-alkyl dimethyl benzyl ammonium chloride, n-alkyl dimethyl ethylbenzyl ammonium chloride, dialkyl dimethyl ammonium chloride, alkyl oxypropyl dihydroxyethyl methyl ammonium chloride and alkyl benzyl imidazolinium chloride. The alkyl groups include substituent hydrocarbon chains from $C_6$ to $C_{20}$, more preferably $C_8$–$C_{18}$, and even more preferably $C_{10}$–$C_{16}$. Substituent hydrocarbon chains with one or more $C_{18}$–$C_{20}$ group result in quaternary ammonium salts with less antimicrobial activity, and these compounds are known to have good fabric softening characteristics.

The anion in the quaternary ammonium compounds is insignificant and can be selected from the group including chloride, sulfates, methosulfates, acetates and bromides. However, in the avenues of trade, the chloride is the most readily available anion offered in the quaternary ammonium compounds. The antimicrobial quaternary ammonium compounds are commercially available typically as liquid solutions and powders. The liquid solutions contain 50 percent to 80 percent by weight active ingredients with the remaining portion of the solution being inert solvents such as water, ethanol, and isopropanol. The powders containing between 40 percent and 100 percent by weight active ingredient with the remainder being an inert water soluble carrier.

Quaternary ammonium compounds in liquid solution or powder form are widely accepted for use as sanitizers and disinfectants. Their use solutions typically have low odor and are not hazardous to the user. Because of their safety, the quaternary ammonium compounds do not have to be rinsed from surfaces prior to food contact. Also, the quaternary ammonium compounds are relatively inexpensive.

Useful phenolic compounds with antimicrobial activity include phenol, p-chlorophenol, dichlorophenol, o-phenylphenol, 2,4,6 trichlorophenol, 2,4,5 trichlorophenol, pentachlorophenol, o-benzyl-p-chlorophenol and para-chloro-meta xylenol. Other substituted phenols may also be appropriate in the solid products of the invention. The substituted phenols would preferably have melting points between 100° F. and 180° F. The alcohol hydrogen in phenol and phenol derivatives is acidic enough to react with certain aqueous bases to form salts containing the phenoxide anion $C_6H_5O$. The neutralized salts or partially neutralized salts can be substituted for the phenolic compounds. The particular cation in the salt forms is irrelevant, and the cations can be sodium, potassium or ammonium among others.

Another class of appropriate antimicrobial agents includes alkyl amines and diamines, for example isodecyl oxypropyl amine acetate, isodecyl oxypropyl diamine, 1-(alkyl-amine)-3-amino propane, sold by AKZO Chemicals under the trade name Duomeen C™ is made from coconut oil and, therefore, has an alkyl chain distribution representative of coconut oil fatty acids. Duomeen C™ is known to be effective against bacteria, fungus and algae. One alkyl group of the appropriate amines and diamines is typically in the range of $C_8$–$C_{18}$.

The particular preferred antimicrobial agent will depend on the method of production and the composition of the final solid product. The composition of the final product will be selected to produce an end use solution with a desired concentration of the antimicrobial compound. If materials are added to dilute the concentrations of antimicrobial compounds, these additives can be inert or selected to provide desired properties to the final composition. For example, additional cleaning agents can be added to the composition to yield an antimicrobial product which cleans as well as disinfects.

In the production of cleaner/disinfectants, surfactants, cheating agents and alkaline builders can be added. The cleaning compositions within the cleaner/disinfectants can be alkaline or neutral pH. A neutral pH cleaning composition would not significantly change the pH of the water used to dilute the product into a final use solution. Tap water will typically range in pH between 5.5 and 8.5. The cleaner/disinfectants are particularly useful for a wide variety of applications usually in the catagory of hard surface cleaning.

Preferred surfactants would be nonionic, although conventional anionic surfactants and cationic surfactants or emulsifiers can be suitable with certain antimicrobial compounds. Conventional anionic surfactants might be compatible with phenolic antimicrobial agents. Concentrations of surfactants in the cleaner/disinfectants will generally be between 10 and 70 percent by weight. In addition, the cleaner/disinfectants can include conventional cleaner additives such as dyes and fragrances.

A variety of nonionic surfactants are known to be useful in cleaners. Nonionic surfactants which can be used in cleaner/disinfectants of the invention include:

Nonylphenol ethoxylates with 4–100 ethylene oxide groups per nonylphenol molecule, i.e., nonylphenol (ethoxylate)$_n$, n=4–100

Dinonylphenol ethoxylates with 4–150 ethylene oxide groups per dinonylphenol molecule Linear alcohol ethoxylates with the alcohol chain consisting of 6–24 carbon atoms and with 2.5 to 150 ethylene oxide groups per alcohol molecule Dodecylphenol ethoxylates with 4–100 ethylene oxide groups per dodecylphenol molecule Octylphenol ethoxylates with 4–100 ethylene oxide groups per octylphenol molecule Alkanolamides in which the carbon chain consists of a $C_{12}$–$C_{18}$ fatty acid reacted with mono or diethanolamine or isopropanolamine to yield a product having a melting point above 100° F.

Ethoxylated alkanolamides in which the carbon chain consists of a $C_{12}$–$C_{18}$ fatty acid reacted with ethylene oxide and mono or diethanolamine or isopropanolamine Amine oxides having a carbon chain from $C_8$ to $C_{18}$ Fatty acid ethoxylates with 2–20 ethylene oxide per fatty acid where the fatty acid has a carbon chain from $C_8$ to $C_{18}$ Ethylene oxide/propylene oxide (eo/po) block copolymers with average molecule weights between 1,000 and 15,000

Nonylphenol ethoxylate propoxylates with average molecular weights between 400–8000

Linear alcohol ethoxylate propxylates with average molecular weights between 400–8000 and carbon chains from $C_8$ to $C_{18}$.

The specific nonionic surfactant will be selected to have the best cleaning properties melting point an dissolving rate for an appropriate cost given the intended use for the cleaning composition. Preferred nonionic surfactants include lower molecular weight nonylphenol ethoxylates and linear alcohol ethoxylates.

Anionic surfactants which could be included in this product include, but are not limited to, all of the following:

1. Alkyl sulfonate salts and alkylaryl sulfonate salts, supplied with the sodium, potassium, ammonium, protonated mono, di or tri-ethanolamine or protonated isoproponolamine cations, such as the following salts:
   Linear primary $C_6$–$C_{18}$ sulfonate salt
   Linear secondary $C_3$–$C_{18}$ sulfonate salt
   Alpha Olefin sulfonate salt
   Dodecylbenzene sulfonate salt
   Tridecylbenzene sulfonate salt
   Xylene sulfonate salt
   Cumene sulfonate salt
   Toluene sulfonate salt 2. Alkyl sulfates salt and alkylaryl sulfate salts, supplied with either Na, K, NH$_4$, protonated mono, di or tri-ethanolamine or protonated isopropanolamine cations, such as the following salts:
   Linear primary $C_6$–$C_{18}$ sulfate salt
   Linear secondary $C_3$–$C_{18}$ sulfate salt
   $C_{12}$–$C_{13}$ benzene sulfate salt 3. Alkyl $C_6$–$C_{18}$ naphthalene sulfonate salts with Na, K or NH$_4$ cations.

4. Alkyl $C_6$–$C_{18}$ diphenyl sulfonate salts with Na, K or NH$_4$ cations.

5. Alkyl ether sulfate salts or alkylaryl ether sulfate salts supplied with Na, K, NH$_4$, protonated mono, di or tri-ethanolamine, or protonated isoproponolamine cations, such as the following salts:
   Alkyl $C_8$–$C_{18}$ alcohol (ethoxylate)$_{1-6}$ sulfate salt.
   Alkyl $C_8$–$C_{12}$ phenoxy (ethoxylate)$_{1-12}$ sulfate salt.

6. Alkyl ether sulfonate salts or alkylaryl ether sulfonate salts supplied with Na, K, NH$_4$, protonated mono, di or tri-ethanolamine or protonated isoproponolamine cations, such as the following salts:
Alkyl $C_8$–$C_{18}$ alcohol (ethoxylate$_{1-6}$ sulfonate salt:
Alkyl $C_8$–$C_{12}$ phenoxy (ethoxylate)$_{1-12}$ sulfonate salt.
7. $C_4$–$C_{18}$ dialkyl sulfosuccinate salts supplied with Na, K, $NH_4$, protonated mono, di or tri-ethanolamine or protonated isoproponolamine cations, such as disodium dioctyl sulfosuccinate.
8. Other anionic surfactants such as mono or dialkyl phosphate ester salts, isothionate or taurate salts.

The choice of anionic surfactant will generally be based on the same factors as the choice of nonionic surfactant.

Cationic emulsifiers are known in the art, and appropriate cationic emulsifiers include isodecyloxypropyl dihydroxyethyl methyl ammonium chloride and isotridecyloxypropyl dihydroxyethyl methyl ammonium chloride, which also exhibit antimicrobial properties.

Alkaline builders are water soluble bases added to cleaning compositions to raise the pH of the resulting cleaning solution. The alkaline builders can have cleaning ability of their own, and they improve the function of the surfactants. The cleaner/disinfectants of this invention include 0 to 60 percent by weight alkaline builder. The amount of alkaline builder in the composition will depend on the relative amounts of cleaning agents desired to achieve the proper cleaning effect. The particular method of production may influence the amount of alkaline builder that can be incorporated into the product.

Powdered, bead, liquid or granular alkaline builders can be used in the formulation of cleaner/disinfectants of the invention. Generally, any water soluble base is appropriate, although certain bases are commonly used as alkaline builders in cleaning compositions. Some alkaline builders that can be included in this product are: sodium or potassium silicate, sodium or potassium carbonate, trisodium or tripotassium phosphate, $Na_2HPO_4$, $K_2HPO_4$, sodium hydroxide potassium hydroxide, monoethanolamine diethanolamine, triethanolamine.

Chelating, sequestering or scale inhibiting ingredients are added to the cleaner to neutralize the adverse consequences of having divalent and trivalent ions of calcium, magnesium, and iron and other less significant polyvalent metal cations in the washing solution. These divalent and trivalent cations enter the cleaning system with the water that is used as the main solvent in washing and rinsing, and with the soils present in the system that are to be removed. These divalent and trivalent ions reduce the effectiveness of cleaning compositions. Subsequent reference to "hardness ions" refers to calcium, magnesium and, to a less degree, iron and other cations which are found in "hard water".

Hardness ions can also precipitate fatty acids present in soils to prevent the solubilization and removal of the fatty acids by the surfactants. Inorganic anions such as carbonate, phosphate, silicate, sulfate, hydroxide and others can precipitate with hardness ions to form inorganic films, spots or deposits on hard surfaces and cleaning machines and devices. The hardness ions can also promote graying and discoloration of fabrics from the deposit of inorganic particles. We use the term sequestering to cover generally chelating and sequestering of polyvalent metal ions that interfere with the cleaning process when free in solution.

Sequestering chemical will prevent these adverse effects because they bind the hardness ions. Binding of the sequestering agent to the ions keeps the hardness ions in solution and prevents the hardness ions from precipitating with the aforementioned organic and inorganic anions. Therefore, addition of sequestering agents prevents mineral scale from building up on cleaning equipment, hard surfaces or fabrics being cleaned and promotes the rinsing of any residual hardness ion/sequestering agent complex that may have dried onto the substrate during the cleaning process.

Sequestering agents will generally be present in the cleaner/disinfectants compositions of the invention at concentrations between 0 and 60 percent by weight of cleaning composition. Well known sequestering agents can be used in the invention, including, but not limited to, the following which are commercially available and commonly used in cleaning formulations:

1. Sodium, potassium, and ammonium salts of orthophosphate or polyphosphates such as pyrophosphate, tripolyphosphate, trimetaphosphate, hexameta phosphate or other higher complex phosphates having up to 22 phosphorus atoms in the anion.
2. Ethylenediamine tetraacetic (EDTA) acid or its fully or partially neutralized salts, e.g., sodium, potassium, ammonium or mono, di or triethanolamine salts.
3. Nitrilotriacetic (NTA) acid $N(CH_2CO_2H)_3$ or its full or partially neutralized salts, e.g., sodium, potassium, ammonium or mono, di or triethanolamine salts.
4. Other aminocarboxylic acids and their salts, for example:
   pentasodium diethylenetriamine pentaacetate
   trisodium hydroxyethyl ethylenediamine triacetate
   disodium ethanoldiglycine
   sodium diethanolglycine
5. Organic polycarboxylic acids and their salts, such as, oxalic acid, citric acid and gluconic acid.
6. Polyacrylic acid polymers and the sodium, potassium, ammonium or mono, di or triethanolamine salts from molecular weight 800 to 50,000.
7. Copolymers, of acrylic and maleic acid and the sodium, potassium, ammonium or mono, di or triethanolamine salts with molecular weights greater than 800.
8. Copolymers, of acrylic acid and itaconic acid and the sodium, potassium, ammonium or mono, di or triethanolamine salts with molecular weights between 800–50,000.
9. Copolymers, of maleic acid and itaconic acid and the sodium, potassium, ammonium or mono, di or triethanolamine salts with molecular weights between 800–50,000.
10. Amino trimethylene phosphonic acid and its sodium, potassium, ammonium or mono, di or triethanolamine salts.
11. 1-Hydroxyethylidine-1, 1-diphosphonic acid and its sodium, potassium, ammonium or mono, di or triethanolamine salts.
12. Hexamethylenediamine tetra(methylenephosphonic acid) and its sodium, potassium, ammonium or mono, di or triethanolamine salts.
13. Diethylene triamine penta(methylene phosphonic acid) and its sodium, potassium, ammonium or mono, di or triethanolamine salts.
14. Dequest 2041™ by Monsanto, which is a similar substituted phosphonic acid or salt.

Inert compounds can also be added to dilute the concentration of the antimicrobial compounds in the final solid product. These inert compounds may be present with the antimicrobial compounds in the liquid or powder form as commercially available. The commercial suppliers may not indicate the chemical composition of the inert compounds. Suitable inert compounds to be added when desired include sodium sulfate, urea, polyethylene glycol, sodium chloride to only mention a few.

Four methods are described below for the production of solid sanitizers within the invention. The first two methods are particularly suitable for the production of disinfectants and sanitizers while the second two are more appropriate for the production of cleaner/disinfectants. Generally, any of the methods could be used to produce sanitizers and cleaner/disinfectants. The choice of antimicrobial agent might also influence the selected method of producing the solid product.

The first method involves the melting of powder antimicrobial compounds or compositions to form a liquid which is poured into an appropriate container or mold where it solidifies upon cooling. Preferred antimicrobial powders will have melting points between about 100° F. and about 300° F. and more preferably between 140° F. and 250° F. Powders with higher melting points yield liquids that are more difficult to handle for commercial production.

It is surprising that powders including quaternary ammonium compounds melt into clear liquids that have good flow properties allowing them to be handled easily and that they are hard waxy solids upon cooling. Pure powders of antimicrobial compounds or powders with inert ingredients can be used within the method. These additional ingredients can be added in powdered form before the heating or in powder or liquid form after the antimicrobial powder is melted.

After the melt is formed, the fluid can be mildly agitated to assure uniform consistency of the liquid. Agitation is continued while any additives are mixed with the melt. The composition may be cooled slightly before pouring to increase the viscosity so that undissolved ingredients will not separate during the packaging, cooling and solidification process. The melt is then poured into a container or a mold where it solidifies upon cooling typically into a hard, waxy solid. Preferably, the melt is poured into a plastic container with a capacity of four fluid ounces to five gallons having an opening at the top between 25 mm and 350 mm wide. A more preferable container would have a capacity of 32 fluid ounces to 192 fluid ounces. The containers are preferably suitable for use in the dispensers described below.

The second method of production uses liquid solutions of antimicrobial compounds. The liquid solutions are heated to evaporate the solvents. The liquid is typically heated to between 120° F. and 300° F. to evaporate the solvent. In a vessel under vacuum, a lower temperature is sufficient. Under atmospheric pressure, a preferred temperature range is between 210° F. and 300° F. Mixing during this evaporation process is desirable especially during the early part of the evaporation.

After the solvent is removed sufficiently, a liquid remains that can be poured into a container or mold similar to the procedure described above with respect to the first method of production. Upon cooling, the liquid forms a stiff paste that does not flow from an inverted open bottle. A small portion of the solvent may be difficult to remove because it binds with the solutes because of hydrogen bonding and other nonbonding interactions. Additives, especially cleaning compounds, can be added to the liquid either before or after heating.

The third method of production uses a meltable solid carrier composition. The carrier is typically heated to a temperature significantly above its melting point, preferably 20° F. or more above its melting point. An antimicrobial powder, liquid or liquid solution is added. The antimicrobial powder can be a pure antimicrobial compound, or it can contain additives. If a liquid solution containing an antimicrobial is used, it should not be added in too large of a quantity such that the solvent interferes with the production process. The mixture is agitated to form a homogeneous liquid. The temperature is kept high enough to keep the mixture a liquid. The liquid is poured into a container or mold as previously described where it hardens into a solid upon cooling.

Many compositions will function as carriers. The preferred materials are water soluble with melting points in the range of 140° F. to 250° F. The carriers can be inert, or they can be cleaning agents, or they can be other antimicrobial compositions. Effective carrier compositions selected to have appropriate melting points include, but are not limited to, surfactants, fatty amines or amine salts such as hexadecylamine and cocoamine acetate, polyethylene glycol (molecular weight>2000), urea and powdered antimicrobial compounds as described above. Additional ingredients such as cleaning compounds can be added either before or after the melt is formed.

A fourth method for producing a solid antimicrobial composition involves a mixture of aqueous liquid antimicrobial solution with an anhydrous or partially hydrated (but further hydratable) neutral or alkaline salt. Appropriate salts include, but are not limited to, sodium tripolyphosphate, sodium trimetaphosphate, sodium sulfate, sodium carbonate, sodium bicarbonate, sodium tetraborate and trisodium phosphate. Other cations can be substituted for sodium cations without affecting the results. They hydratable salt is added to a powder mixer, such as a ribbon mixer or paddle mixture, and the mixer is started. The liquid antimicrobial solution is added to the powdered salt until a flowable semi-liquid (thin paste) consistency develops.

The resulting semi-liquid (thin paste like) mixture is poured into a container or a mold and stored. The water supplied with the aqueous antimicrobial solution hydrates the alkaline salt to form a rigid cake. The hydration process to form the solid typically takes one to three days. A variation on this process involves the substitution of a powder antimicrobial and water for the aqueous antimicrobial solution. The powder antimicrobial, the powder salt and the water are mixed to form the semi-liquid mixture. In any of the variations noted above, reasonable amounts of other additives can be added to the semi-liquid mixture in the formation of the solid product.

The solid compositions of the invention can be molded into tablets for use. For example, these tablets can be formed in premeasured quantities. The tablets would be dissolved in water to form a sanitizing solution for appropriate applications. Tablets are not the preferred form of the product because they generally dissolve slowly. It is more preferred to form the solid in a container that can be used in an appropriate dispenser. The dispensers facilitate the dissolving of the product.

Typically, the container 10 will be generally cylindrical with a tapered portion 12 ending at an opening 14. Referring to FIG. 1, the dispenser 16 will have a bowl 18 into which the container 10 is inverted. The bottom 20 of bowl 18 has a funnel shape to direct solutions into tubing 22 attached at the end of the funnel shaped bottom 20 of bowl 18. A spray tip 24 projects into the funnel portion 20 of the bowl 18. The spray tip 24 is placed such that it will spray water into container 10 to dissolve a portion of the product within container 10. The funnel 20 can direct the solution into tubing 22.

A specific example of a particularly suitable dispenser is described in U.S. Pat. No. 5,342,587 to Laughlin et al. In this dispenser, a water inlet is attached to a fitting with a secondary outlet that directs a portion of water to a spray tip within the dispenser bowl. In one embodiment, the primary outlet of the fitting goes to an inlet to a Y-fitting that has a second inlet connected to the funnel at the end of the bowl. The outlet to the Y-fitting can be connected to the end of a hose. Using this dispenser, an antimicrobial agent stored as a solid in the container can be selectively added to a stream of water that is directed out the end of a hose. This is particularly convenient for sanitizing a large area which can be hosed down with a sanitizer dispensed from the end of the hose. For smaller applications, the hose can be directed into a bucket or a similar container. Other designs for dispensers can also be used.

EXAMPLE 1

A 200 g sample of powdered n-alkyl dimethyl benzyl ammonium chloride dihydrate, sold by Crystal Performance Chemicals under the trademark JAQ Powdered Quat™ is placed in a 600 ml beaker. This quaternary ammonium composition has an approximate distribution of alkyl chain lengths of $C_{16}$ 2 percent, $C_{14}$ 95 percent and $C_{12}$ 3 percent and is known to have antimicrobial properties. The beaker containing the powder is heated on a hot plate to 160° F. with occasional stirring with a propeller-type agitator. The powder melted into a liquid. The liquid quaternary ammonium composition was poured into an eight ounce bottle. Upon cooling, the composition solidified.

EXAMPLE 2

A 200 g sample of TBC2125MP40™ sold by Stepan Chemical Company is placed in a 600 ml beaker. BTC2125MP40 contains 20 percent n-alkyl dimethyl benzyl ammonium chloride ($C_{12}$ 5 percent, $C_{14}$ 60 percent, $C_{16}$ 30 percent, $C_{18}$ 5 percent), 20 percent n-alkyl dimethyl ethyl benzyl ammonium chloride ($C_{12}$ 68 percent, $C_{14}$ 32 percent) and 60 percent inert ingredients. The quaternary ammonium salts are known to have antimicrobial properties. The beaker is heated to 250° F. where the powder melts to form a liquid. The melted composition was poured into an eight ounce bottle where it solidified upon cooling.

EXAMPLE 3

A mixture of 100 g of powder N-coco-1,3 diaminopropane (Duomeen C™ sold by AKZO) and 100 g of flaked coco monoethanolamine (Alkamide L203™ sold by Rhone Poulenc) is placed into a beaker. The Duomeen C™ is known to have antimicrobial activity. The mixture is heated to a temperature of 190° F. where the mixture is liquid. The melted mixture is poured into an eight fluid ounce bottle where it solidifies upon cooling.

EXAMPLE 4

A 200 g sample of powder orthobenzyl parachlorophenol with known antimicrobial properties is placed into a beaker. The sample is heated slowly on a hot plate to 120° F. to form a liquid upon melting the orthobenzyl parachlorophenol. The liquid is poured into an eight fluid ounce plastic bottle. Upon cooling, the compound forms a solid in the bottle.

EXAMPLE 5

This example describes the production of a solid antimicrobial cleaning product. About 67.6 g of JAQ™ brand n-alkyl dimethyl benzyl ammonium chloride dihydrate ($C_{16}$ 2 percent, $C_{14}$ 95 percent and $C_{12}$ 3 percent), 27.8 g of nonylphenol (ethoxylate)$_{12}$, sold by Harcross under the trademark T-DET N-12™, and 30.0 g tetrasodium ethylenediaminetetraacetate (EDTA) were heated together in a beaker to a temperature of 160° F. The mixture was stirred with a propeller type mixer until fluid. While continuing agitation, the mixture was allowed to cool to 140° F. At 140° F. the mixture was poured into a plastic 76 fluid oz. bottle to solidify.

EXAMPLE 6

A sample of 500 grams of FMB451-8 Quat™ is placed into a 1000 ml beaker. FMB451-8 Quat™ is a liquid antimicrobial product containing 80 percent by weight n-alkyl dimethyl benzyl ammonium chloride ($C_{12}$ 40 percent;, $C_{14}$ 50 percent and $C_{16}$ 10 percent) 12.5 percent ethanol and 7.5 percent water. The beaker containing the liquid was placed on a hot plate and heated first to 98° C. where it started boiling. The heat was slowly raised to a maximum of 150° C. After a temperature of 150° C. is reached, this temperature is maintained for 30 minutes while solvent continued to boil off.

After this period of boiling, the beaker is removed from the heat and allowed to cool to 100° C. The liquid becomes more viscous as it cools. Then, the product is poured into a plastic 32 fluid oz. bottle. In the bottle, the composition cools to form a highly viscous gel-like substance that does not flow unless agitated. The final product has a weight of about 400 g indicating the loss of about 100 g of solvent from the evaporation process. This indicates that essentially all of the solvent initially present in the liquid antimicrobial product is removed by the heating process.

EXAMPLE 7

A 350 g sample of sodium tripolyphosphate was placed into a mixing vessel. A 280 g sample of liquid antimicrobial composition FMB1210-50™ sold by Crystal Performance Chemicals was added to the mixing vessel. FMB1210-50™ contains about 50 percent by weight water and 30 percent didecyl dimethyl ammonium chloride and 20 percent n-alkyl dimethyl benzyl ammonium chloride ($C_{12}$ 40 percent, $C_{14}$ 50 percent, $C_{16}$ 10 percent). The mixture was mixed in a paddle mixer until a free flowing but viscous blend was formed. The mixture was poured into a 76 fluid oz. plastic bottle. After standing for three days at room temperature, the composition has formed a solid.

EXAMPLE 8

The composition of Example 1 is prepared in a bottle. The bottle is placed in a dispenser similar to the dispenser shown in FIG. 1. An upward water spray dissolves a portion of the composition which is collected when draining out of the funnel. The solution draining out of the funnel contains 0.4750% or 4750 ppm of the quaternary ammonium salt as determined by titration using a commercially available test kit, for example, Taylor's™ test kit, K-1582 QAC(High) test™.

The solution is to be used as a sanitizer in a food handling operation, so the desired concentration of the quaternary ammonium salt is nominally 200 ppm. To achieve the proper concentration, the solution is collected in a gallon jug as it drains from the funnel. A 5.5 fluid ounce quantity of the concentrate from the funnel is diluted to 1 gallon of water to achieve the 200 ppm concentration desired. The final solution is sprayed onto pre-cleaned surfaces to kill any microorganisms that remain after cleaning.

EXAMPLE 9

Again, the composition of Example 1 is prepared in a bottle. The bottle is placed in a dispenser where the bowl connects with a fresh water supply as claimed in U.S. Pat. No. 5,342,587 to Laughlin et al. The dispenser directs water at the solid composition to dissolve a portion of the composition. The concentrated solution draining from the bowl is mixed with fresh water from a hose to form a diluted solution that flows through a dispensing hose. The relative flow to the spray nozzle and the hose stream is adjusted to yield a 200 ppm solution as it exits the dispensing hose. The resulting solution is sprayed from the dispensing hose onto surfaces to be sanitized, such as equipment, tables and fixtures in a food processing plant.

EXAMPLE 10

The cleaner/disinfecting composition of Example 5 is prepared in a bottle. The bottle is inverted over a dispenser where the bowl connects with a fresh water supply as claimed in U.S. Pat. No. 5,342,587. A water spray dissolves a portion of the composition to form a solution which drains from the bowl. The concentrated solution combines with a connecting flow of clean water after leaving the bowl. The relative flow to the spray nozzle and the hose stream is adjusted to yield a 600 ppm solution as it exits the dispensing hose. The concentration of quaternary ammonium salt is determined using a commercial test kit, as previously described. The dispensing hose can be used to deliver cleaner/disinfecting solution to a mop bucket for mopping floors or to another container such as a spray bottle. Mopping floors with this solution removes soils while leaving an antimicrobial residue. The antimicrobial residue can destroy any microbes left on the floor, reduce odors and prohibit the transmission of disease caused by pathogenic organisms.

I claim:

1. An article of manufacture, comprising:
a container opened at its opening and inverted in a bowl of a dispenser, the dispenser configured to be connected to a water supply, with a drain at the bottom of the bowl, and a spray nozzle for directing water from the water supply upward from the bowl and into the opening of the container; and
a nonflowable solid antimicrobial composition solidified in the container from a melt, and consisting essentially of between about 0.02 to 99.98% by weight of a quaternary ammonium compound with antimicrobial properties, urea, and optionally an additive selected from the group consisting of a fragrance and a dye.

2. The article of claim 1, in which a portion of the container tapers toward the opening.

3. The article of claim 1, in which the quaternary ammonium compound includes a quaternary nitrogen atom and at least one substituent alkyl group bonded to the quaternary nitrogen atom, the substituent alkyl group with a chain length between about $C_6$ and $C_{20}$.

4. The article of claim 1, in which the quaternary ammonium compound is present in an amount greater than about 0.02% by weight.

5. The article of claim 1, in which the quaternary ammonium compound is present in an amount greater than about 5% by weight.

6. The article of claim 1, in which the quaternary ammonium compound is present in an amount between about 5% and 40% by weight.

7. The article of claim 1, in which the urea is present in a greater amount than the quaternary ammonium compound.

8. An article of manufacture, comprising:
a container opened at its opening and inverted in a bowl of a dispenser, the dispenser configured to be supplied with water from a water source and including a drain at a bottom portion of the bowl and a spray nozzle for directing water from the water source upward from the bowl and into the opening of the container; and
a nonflowable solid antimicrobial composition solidified in the container from a melt and consisting of urea and between about 0.02 and 99.98% by weight of a quaternary ammonium compound with antimicrobial properties, and optionally a fragrance or a dye.

9. The article of claim 8, in which the quaternary ammonium compound includes at least one substituent alkyl group with a chain length between about $C_6$ and $C_{20}$.

10. The article of claim 8, in which the quaternary ammonium compound is present in an amount between about 5 and 99.98% by weight.

11. The article of claim 8, in which the quaternary ammonium compound is present in an amount between about 5% and 40% by weight.

12. The article of claim 8, in which the urea is present in a greater amount than the quaternary ammonium compound.

13. An article of manufacture, comprising:
a container that is opened at its opening and inverted into a bowl of a dispenser, the dispenser configured to be connected to a water supply and having a drain at the bottom of the bowl, wherein the dispenser includes a spray nozzle for directing water from the water supply upward from the bowl and into the container opening; and
a nonflowable solid antimicrobial composition solidified in the container from a melt, the solid composition consisting of between about 0.02 and 99.98 percent by weight of a quaternary ammonium compound with antimicrobial properties and urea and optionally an additive selected from a fragrance and a dye.

14. The article of claim 13, in which the quaternary ammonium compound includes a quaternary nitrogen atom and at least one substituent alkyl group bonded to the quaternary nitrogen atom, the substituent alkyl group with a chain length between about $C_6$ and $C_{20}$.

15. The article of claim 13, in which the quaternary ammonium compound is present in an amount between about 5 and 99.98% by weight.

16. The article of claim 13, in which the quaternary ammonium compound is present in an amount between about 5% and 40% by weight.

17. The article of claim 13, in which the urea is present in a greater amount than the quaternary ammonium compound.

18. A method of forming an antimicrobial solution, comprising:
providing an article comprising:
a container with an opening; and
a nonflowable, solid, and homogeneous antimicrobial composition solidified from a melt in the container and consisting essentially of between about 0.02 to 99.98 percent by weight of a quaternary ammonium compound with antimicrobial properties, urea, and optionally a fragrance or a dye;
placing the container and solid composition into a dispenser bowl of a dispenser, the dispenser bowl accommodating the inverted container, the dispenser having tubing depending from the bowl and a spray tip proximate the bowl; and
impinging a surface of the composition with a generally upwardly directed spray of water from the spray tip through the container opening, thereby dissolving a portion of the composition and forming a first antimicrobial solution.

19. The method of claim 18, in which a quaternary ammonium concentration of the first antimicrobial solution is between about 200 ppm and 4750 ppm.

20. The method of claim 18, in which a quaternary ammonium concentration of the first antimicrobial solution is between about 200 ppm and 600 ppm.

21. The method of claim 18, in which a quaternary ammonium concentration of the first antimicrobial solution is between about 600 ppm and 4750 ppm.

22. The method of claim 18, further comprising diluting the first antimicrobial solution with water to form a second antimicrobial solution.

23. The method of claim 22, in which a quaternary ammonium concentration of the second antimicrobial solution is between about 200 ppm and 600 ppm.

24. A method of making an article of manufacture, comprising:

providing a dispenser connected to a water supply and including a drain in a bottom portion of a bowl and a spray nozzle connected to the water supply;

melting a substance consisting essentially of between about 0.02 to 99.98 weight percent of a quaternary ammonium compound with antimicrobial properties, urea, and optionally an additive selected from the group consisting of a fragrance and a dye;

pouring the melted substance in a container and solidifying the melted substance in the container, thereby forming a nonflowable solid antimicrobial composition in the container; and inverting the container in the bowl of the dispenser, the inverted container in the dispenser bowl defining an opening positioned to receive a generally upwardly directed spray delivered from the water supply through the spray nozzle.

* * * * *